United States Patent
Chinachoti et al.

(10) Patent No.: US 10,849,338 B2
(45) Date of Patent: Dec. 1, 2020

(54) PET FOOD COMPOSITIONS INCLUDING PROBIOTICS AND METHODS OF MANUFACTURE AND USE THEREOF

(71) Applicant: Hill's Pet Nutrition, Inc., Topeka, KS (US)

(72) Inventors: Pavinee Chinachoti, Songkhla (TH); Kathy Gross, Topeka, KS (US); Christina Khoo, Duxbury, MA (US); Luis Montelongo, Lawrence, KS (US)

(73) Assignee: Hills Pet Nutrition, Inc., Topeka, KS (US)

( * ) Notice: Subject to any disclaimer, the term of this patent is extended or adjusted under 35 U.S.C. 154(b) by 0 days.

(21) Appl. No.: 16/247,629

(22) Filed: Jan. 15, 2019

(65) Prior Publication Data

US 2019/0142032 A1 May 16, 2019

Related U.S. Application Data

(62) Division of application No. 13/516,302, filed as application No. PCT/US2009/068695 on Dec. 18, 2009, now Pat. No. 10,212,954.

(51) Int. Cl.
A23K 50/42 (2016.01)
A23K 40/25 (2016.01)
A23K 40/20 (2016.01)
A23K 10/18 (2016.01)

(52) U.S. Cl.
CPC ............ *A23K 50/42* (2016.05); *A23K 10/18* (2016.05); *A23K 40/20* (2016.05); *A23K 40/25* (2016.05); *A23V 2002/00* (2013.01)

(58) Field of Classification Search
None
See application file for complete search history.

(56) References Cited

U.S. PATENT DOCUMENTS

| | | | |
|---|---|---|---|
| 5,968,569 A | 10/1999 | Cavadini et al. |
| 6,254,910 B1 | 7/2001 | Paluch |
| 6,500,426 B1 | 12/2002 | Barendse et al. |
| 2005/0064073 A1 | 3/2005 | Paluch et al. |
| 2005/0153018 A1 | 7/2005 | Ubbink et al. |

FOREIGN PATENT DOCUMENTS

| | | |
|---|---|---|
| WO | WO 1999/048372 | 9/1999 |
| WO | WO 2001/025414 | 4/2001 |
| WO | WO 2001/090311 | 11/2001 |

OTHER PUBLICATIONS

Amara et al. (Saudi Pharmaceutical Journal vol. 23 No. 2, pp. 107-114).*

* cited by examiner

*Primary Examiner* — Robert A Zeman (57) ABSTRACT

The present invention encompasses pet food compositions that include one or more probiotic microorganisms, which are useful to improve the health of companion animals. For example, the invention encompasses pet food compositions including a probiotic, for example, *Lactobacillus, Bifidobacterium* and *Streptococcus* (*Enterococcus*). The present invention also encompasses the preparation of pet food compositions including one or more probiotic microorganisms intended for methods of maintaining or improving pet health through feeding a pet a pet food composition including the probiotic microorganism.

8 Claims, 3 Drawing Sheets

PET FOOD COMPOSITIONS INCLUDING PROBIOTICS AND METHODS OF MANUFACTURE AND USE THEREOF

BACKGROUND OF THE INVENTION

The well-being of domestic animals is closely related to their feeding. Correct feeding should result in a fit and healthy pet. In addition to providing nutritional value, food compositions influence the intestinal microflora equilibrium and may lead to or prevent gastrointestinal disorders.

As meat-eaters, cats and dogs are characterized by a short digestive tract and a rapid flow rate of the bolus of food. Among the constituents of the gastrointestinal microflora of cats and dogs, *Bacteroides* sp., *Clostridium* sp., Enterobacteriaceae, *Bifidobacterium* sp., *Lactobacillus* sp., *Streptococcus* sp., *Staphylococcus* sp. and yeasts can be recovered. The number and composition of this endogenous flora tend to be rather stable, although age and, to a lesser degree, food, may modify it. Gastric acidity, bile, intestinal peristalsis and local immunity are factors thought to be important in the regulation of bacterial flora in the small intestine of human beings and various other mammals. Often canine and feline gastrointestinal disorders are linked to irregular bacterial growth and the production of enterotoxins produced by pathogenic bacteria.

Probiotics promote heath benefits for people and animals. However, current extrusion conditions are detrimental for probiotics because they are sensitive to harsh processing and storage conditions. Therefore, gentler processing conditions can improve probiotics survival-ability.

The invention encompasses cold extrusion technology to improve probiotic, for example, *Lactobacillus acidophilus*, stability. It was found that making cold pellets preserved *L. acidophilus* better than hot pellets. Consequently, the inventors have identified compositions and methods wherein one or more probiotic microorganisms are incorporated in pet food compositions to improve companion animal health.

SUMMARY OF THE INVENTION

The invention encompasses pet food compositions comprising a starch source and one or more live probiotic microorganisms.

In certain embodiments, the starch source preferably has a degree of gelatinization less than about 7.5 Joules/g of starch.

In certain embodiments, the starch source is substantially non-gelatinized.

The invention encompasses methods of making cold pellets preserved probiotics, for example, *L. acidophilus*, better than hot pellets process. For example, the inventors have found that improvement of cold pellets process (e.g., a gentler drying) should improve the probiotic retention; the hot pellets show a faster disappearance of probiotics than the cold pellets.

In certain embodiments, topical coating resulted in the best retention (only 0.5 log cycle loss of activity) than when it was added to the grain mix. In certain embodiments, topical coating also showed a far better stability than addition to the grain mix.

In certain embodiments, process improvement is possible by controlling the moisture, shear and temperature during the process of cold pellets (e.g., use of a low-shear pelletizer).

In certain embodiments, the live probiotic microorganism included within the composition of the invention is one or more of the genera: *Bifidobacterium*, *Bacteroides*, *Clostridium*, *Fusobacterium*, *Melissococcus*, *Propionibacterium*, *Streptococcus*, *Enterococcus*, *Lactococcus*, *Staphylococcus*, *Peptostrepococcus*, *Bacillus*, *Pediococcus*, *Micrococcus*, *Leuconostoc*, *Weissella*, *Aerococcus*, *Oenococcus*, or *Lactobaccillus*.

In another embodiment, the invention encompasses a method for making a pet food composition comprising one or more probiotics comprising the steps of:
(1) mixing the following:
  (a) poultry meal and/or soybean meal;
  (b) one or more probiotics;
(2) adding a starch source and water with mixing;
(3) extruding the mixture at a temperature below about 70° C.; and
(4) drying the material at a temperature of below about 70° C.

In certain embodiments, the starch source preferably has a degree of gelatinization less than about 7.5 Joules/g of starch. In certain embodiments, the starch source is substantially non-gelatinized.

In another embodiment, the invention encompasses methods for maintaining the health of a gastrointestinal tract of a companion pet comprising administering an effective amount of a pet food composition comprising a starch source and one or more live probiotic microorganisms, wherein the starch source has a degree of gelatinization less than about 7 Joules/g of starch and wherein the live probiotic microorganism is one or more of the genera: *Bifidobacterium*, *Bacteroides*, *Clostridium*, *Fusobacterium*, *Melissococcus*, *Propionibacterium*, *Streptococcus*, *Enterococcus*, *Lactococcus*, *Staphylococcus*, *Peptostrepococcus*, *Bacillus*, *Pediococcus*, *Micrococcus*, *Leuconostoc*, *Weissella*, *Aerococcus*, *Oenococcus*, or *Lactobaccillus*.

In another embodiment, the invention encompasses methods for maintaining the health of skin and/or a coat of a companion pet comprising an administering an effective amount of a pet food composition comprising a starch source and one or more live probiotic microorganisms, wherein the starch source has a degree of gelatinization less than about 7 Joules/g of starch and wherein the live probiotic microorganism is one or more of the genera: *Bifidobacterium*, *Bacteroides*, *Clostridium*, *Fusobacterium*, *Melissococcus*, *Propionibacterium*, *Streptococcus*, *Enterococcus*, *Lactococcus*, *Staphylococcus*, *Peptostrepococcus*, *Bacillus*, *Pediococcus*, *Micrococcus*, *Leuconostoc*, *Weissella*, *Aerococcus*, *Oenococcus*, or *Lactobaccillus*.

In another embodiment, the invention encompasses methods for regulating an immune system of a companion pet comprising administering an effective amount of a pet food composition comprising a starch source and one or more live probiotic microorganisms, wherein the starch source has a degree of gelatinization less than about 7 Joules/g of starch and wherein the live probiotic microorganism is one or more of the genera: *Bifidobacterium*, *Bacteroides*, *Clostridium*, *Fusobacterium*, *Melissococcus*, *Propionibacterium*, *Streptococcus*, *Enterococcus*, *Lactococcus*, *Staphylococcus*, *Peptostrepococcus*, *Bacillus*, *Pediococcus*, *Micrococcus*, *Leuconostoc*, *Weissella*, *Aerococcus*, *Oenococcus*, or *Lactobaccillus*.

In another embodiment, the invention encompasses methods for ameliorating or reducing effects of aging in a companion pet comprising an administering an effective amount of a pet food composition comprising a starch source and one or more live probiotic microorganisms, wherein the starch source has a degree of gelatinization less than about 7 Joules/g of starch and wherein the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus*, or *Lactobaccillus*.

DETAILED DESCRIPTION OF THE INVENTION

The invention generally encompasses pet food compositions comprising a starch source and a live probiotic microorganism, wherein the starch source has a degree of gelatinization less than about 7.5 Joules/g of starch and wherein the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus*, or *Lactobaccillus*.

In certain embodiments, the starch source is substantially non-gelatinized.

In certain embodiments, the probiotic is included in the pet food in an amount of about $10^4$ cfu/g of pet food to about $10^{14}$ cfu (colony forming units)/g of pet food.

In certain embodiments, the composition further comprises at least one protein source.

In certain embodiments, the composition further comprises at least one source of fat.

In certain embodiments, the composition further comprises at least one carbohydrate source.

In certain embodiments, the pet food is a dog food.

In certain embodiments, the pet food is a cat food.

In certain embodiments, the probiotic microorganism is *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcusfaecalis, Lactobacillus bulgaricus, Lactobacillus acidophilus, Lactobacillus alimentarius, Lactobacillus casei* subsp. *casei, Lactobacillus casei Shirota, Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus reuteri, Lactobacillus rhamnosus (Lactobacillus GG), Lactobacillus sake, Lactobacillus sporogenes, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Streptococcus faecium, Staphylococcus carnosus, Leuconostoc mesenteroides* ssp *cremoris, Pediococcus acidolactici, Pediococcus cerevisiae, Bifidobacterium bifidus, Bifidobacterium longum, Brevibacterium linens, Propionibacterium shermanii, Propionibacterium arabinosum, Penicillium roquefortii, Penicillium camembertii*, or *Staphylococcus xylosus*.

In certain embodiments, the pet food comprises a binding agent.

In certain embodiments, the binding agent is sodium alginate, gum arabic, sodium carboxymethyl cellulose, guar gum, xanthan gum, maltodextrin, pregelatinized starch and a soy protein binder.

In another embodiment, the invention encompasses methods for maintaining the health of a gastrointestinal tract of a companion pet comprising an administering an effective amount of a pet food composition comprising a starch source and a live probiotic microorganism, wherein the starch source has a degree of gelatinization less than about 7 Joules/g of starch and wherein the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus*, or *Lactobaccillus*.

In certain embodiments, the starch source is substantially non-gelatinized.

In certain embodiments, the probiotic is present in the pet food in an amount of about $10^4$ cfu/g of pet food to about $10^{14}$ cfu/g of pet food.

In certain embodiments, the composition further comprises at least one protein source.

In certain embodiments, the composition further comprises at least one source of fat.

In certain embodiments, the composition further comprises at least one carbohydrate source.

In certain embodiments, the pet food is a dog food.

In certain embodiments, the pet food is a cat food.

In certain embodiments, the probiotic microorganism is *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcusfaecalis, Lactobacillus bulgaricus, Lactobacillus acidophilus, Lactobacillus alimentarius, Lactobacillus casei* subsp. *casei, Lactobacillus casei Shirota, Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus reuteri, Lactobacillus rhamnosus (Lactobacillus GG), Lactobacillus sake, Lactobacillus sporogenes, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Streptococcus faecium, Staphylococcus carnosus, Leuconostoc mesenteroides* ssp *cremoris, Pediococcus acidolactici, Pediococcus cerevisiae, Bifidobacte-* rium bifidus, Bifidobacterium longum, Brevibacterium linens, Propionibacterium shermanii, Propionibacterium arabinosum, Penicillium roquefortii, Penicillium camembertii, or Staphylococcus xylosus.

In certain embodiments, the pet food comprises a binding agent.

In certain embodiments, the binding agent is sodium alginate.

In another embodiment, the invention encompasses methods for maintaining the health of skin and/or a coat of a companion pet comprising an administering an effective amount of a pet food composition comprising a starch source and a live probiotic microorganism, wherein the starch source has a degree of gelatinization less than about 7.5 Joules/g of starch and the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus,* or *Lactobaccillus.*

In certain embodiments, the starch source is substantially non-gelatinized.

In certain embodiments, the probiotic is present in the pet food in an amount of about $10^4$ cfu/g of pet food to about $10^{14}$ cfu/g of pet food.

In certain embodiments, the composition further comprises at least one protein source.

In certain embodiments, the composition further comprises at least one source of fat.

In certain embodiments, the composition further comprises at least one carbohydrate source.

In certain embodiments, the pet food is a dog food.

In certain embodiments, the pet food is a cat food.

In certain embodiments, the probiotic microorganism is *Saccharomyces* cereviseae, *Bacillus coagulans, Bacillus licheniformis, Bacillus subtilis, Bifidobacterium bifidum, Bifidobacterium infantis, Bifidobacterium longum, Enterococcus faecium, Enterococcusfaecalis, Lactobacillus bulgaricus, Lactobacillus acidophilus, Lactobacillus alimentarius, Lactobacillus casei* subsp. *casei, Lactobacillus casei Shirota, Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus reuteri, Lactobacillus rhamnosus (Lactobacillus GG), Lactobacillus sake, Lactobacillus sporogenes, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Streptococcus faecium, Staphylococcus carnosus, Leuconostoc mesenteroides* ssp *cremoris, Pediococcus acidolactici, Pediococcus cerevisiae, Bifidobacterium bifidus, Bifidobacterium longum, Brevibacterium linens, Propionibacterium shermanii, Propionibacterium arabinosum, Penicillium roquefortii, Penicillium camembertii,* or *Staphylococcus xylosus.*

In certain embodiments, the pet food comprises a binding agent.

In certain embodiments, the binding agent is sodium alginate.

In another embodiment, the invention encompasses methods for regulating an immune system of a companion pet comprising an administering an effective amount of a pet food composition comprising a starch source and a live probiotic microorganism, wherein the starch source has a degree of gelatinization less than about 7.5 Joules/g of starch and wherein the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus,* or *Lactobaccillus.*

In certain embodiments, the starch source is substantially non-gelatinized.

In certain embodiments, the probiotic is present in the pet food in an amount of about $10^4$ cfu/g of pet food to about $10^{14}$ cfu/g of pet food.

In certain embodiments, the composition further comprises at least one protein source.

In certain embodiments, the composition further comprises at least one source of fat.

In certain embodiments, the composition further comprises at least one carbohydrate source.

In certain embodiments, the pet food is a dog food.

In certain embodiments, the pet food is a cat food.

In certain embodiments, the probiotic microorganism is *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcusfaecalis, Lactobacillus bulgaricus, Lactobacillus acidophilus, Lactobacillus alimentarius, Lactobacillus casei* subsp. *casei, Lactobacillus casei Shirota, Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus reuteri, Lactobacillus rhamnosus (Lactobacillus GG), Lactobacillus sake, Lactobacillus sporogenes, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Streptococcus faecium, Staphylococcus carnosus, Leuconostoc mesenteroides* ssp *cremoris, Pediococcus acidolactici, Pediococcus cerevisiae, Bifidobacterium bifidus, Bifidobacterium longum, Brevibacterium linens, Propionibacterium shermanii, Propionibacterium arabinosum, Penicillium roquefortii, Penicillium camembertii,* or *Staphylococcus xylosus.*

In certain embodiments, the pet food comprises a binding agent.

In certain embodiments, the binding agent is sodium alginate.

In another embodiment, the invention encompasses methods for ameliorating or reducing effects of aging in a companion pet comprising an administering an effective amount of a pet food composition comprising a starch source and a live probiotic microorganism, wherein the starch source has a degree of gelatinization less than about 7.5 Joules/g of starch and wherein the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus,* or *Lactobaccillus.*

In certain embodiments, the starch source is substantially non-gelatinized.

In certain embodiments, the probiotic is in an amount of about $10^4$ cfu/g of pet food to about $10^{14}$ cfu/g of pet food.

In certain embodiments, the composition further comprises at least one protein source.

In certain embodiments, the composition further comprises at least one source of fat.

In certain embodiments, the composition further comprises at least one carbohydrate source.

In certain embodiments, the pet food is a dog food.

In certain embodiments, the pet food is a cat food.

In certain embodiments, the probiotic microorganism is *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcusfaecalis, Lactobacillus bulgaricus, Lactobacillus acidophilus, Lactobacillus alimentarius, Lactobacillus casei* subsp. *casei, Lactobacillus casei Shirota, Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus reuteri, Lactobacillus rhamnosus (Lactobacillus GG), Lactobacillus sake, Lactobacillus sporogenes, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Streptococcus faecium, Staphylococcus carnosus, Leuconostoc mesenteroides* ssp *cremoris, Pediococcus acidolactici, Pediococcus cerevisiae, Bifidobacterium bifidus, Bifidobacterium longum, Brevibacterium linens, Propionibacterium shermanii, Propionibacterium arabinosum, Penicillium roquefortii, Penicillium camembertii,* or *Staphylococcus xylosus.*

In certain embodiments, the pet food comprises a binding agent.

In certain embodiments, the binding agent is sodium alginate.

Compositions of the Invention

The invention generally encompasses pet food compositions comprising a starch source and a live probiotic microorganism, wherein the starch source has a degree of gelatinization less than about 7.5 Joules/g of starch and wherein the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus,* or *Lactobaccillus.*

In certain embodiments, the starch source is substantially non-gelatinized.

In certain embodiments, the probiotic is present in the pet food in an amount of about $10^4$ cfu/g of pet food to about $10^{14}$ cfu/g of pet food.

In certain embodiments, the composition further comprises at least one protein source.

In certain embodiments, the composition further comprises at least one source of fat.

In certain embodiments, the composition further comprises at least one carbohydrate source.

In certain embodiments, the pet food is a dog food.

In certain embodiments, the pet food is a cat food.

In certain embodiments, the probiotic microorganism is *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcusfaecalis, Lactobacillus bulgaricus, Lactobacillus acidophilus, Lactobacillus alimentarius, Lactobacillus casei* subsp. *casei, Lactobacillus casei Shirota, Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus reuteri, Lactobacillus rhamnosus (Lactobacillus GG), Lactobacillus sake, Lactobacillus sporogenes, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Streptococcus faecium, Staphylococcus carnosus, Leuconostoc mesenteroides* ssp *cremoris, Pediococcus acidolactici, Pediococcus cerevisiae, Bifidobacterium bifidus, Bifidobacterium longum, Brevibacterium linens, Propionibacterium shermanii, Propionibacterium arabinosum, Penicillium roquefortii, Penicillium camembertii,* or *Staphylococcus xylosus.*

In certain embodiments, the pet food comprises a binding agent.

In certain embodiments, the binding agent is sodium alginate.

In certain embodiments, the pet food composition is in the form of a kibble.

In certain embodiments, the pet food composition is in the form of a pet snack.

In another embodiment, the invention encompasses a dried, ready-to-eat pet food composition comprising:
 (i) a starch source, wherein the starch source has a degree of gelatinization less than about 7.5 Joules/g of starch;
 (ii) a coating or filling including one or more probiotic microorganisms.

In certain embodiments, the starch source is substantially non-gelatinized.

In certain embodiments, the starch source is a cooked starch which is cooked at a low temperature (i.e., <60° C.).

In certain embodiments, the coating comprises a carrier substrate which contains one or more probiotic microorganisms.

In certain embodiments, the carrier substrate is at least one carrier chosen from the group consisting of a fat, a protein digest, milk solids, a sugar and a particulate flavoring agent.

In certain embodiments, the pet food composition further includes a source of soluble fiber.

In certain embodiments, the pet food composition comprises a binding agent.

In certain embodiments, the binding agent is sodium alginate.

In another embodiment the invention encompasses a dried, ready-to-eat pet food composition comprising:
 (i) a starch source which includes a protein source, wherein the starch source has a degree of gelatinization less than about 7.5 Joules/g of starch;
 (ii) a coating or a filling containing one or more probiotic microorganisms.

In certain embodiments, the starch source is substantially non-gelatinized.

In certain embodiments, the coating or filling comprises a carrier substrate which contains the one or more probiotic microorganisms.

In certain embodiments, the carrier substrate is a fat, or a protein digest, or a mixture thereof.

In certain embodiments, the pet food composition further includes a source of soluble fiber.

In certain embodiments, the pet food composition comprises a binding agent.

In certain embodiments, the binding agent is sodium alginate.

In another embodiment, the invention encompasses a dried, ready-to-eat pet food in the form of kibbles, each kibble comprising:

(i) a starch source, wherein the starch source has a degree of gelatinization less than about 7.5 Joules/g of starch;
(ii) a coating or filling including one or more probiotic microorganisms.

In certain embodiments, the starch source is substantially non-gelatinized.

In certain embodiments, the starch source is a starch which is cooked at a low temperature (i.e., <60° C.).

In certain embodiments, the coating comprises a carrier substrate which contains one or more probiotic microorganisms.

In certain embodiments, the carrier substrate is at least one carrier chosen from the group consisting of a fat, a protein digest, milk solids, a sugar and a particulate flavoring agent.

In certain embodiments, the pet kibble further includes a source of soluble fiber.

In certain embodiments, the pet kibble comprises a binding agent.

In certain embodiments, the binding agent is sodium alginate.

In another embodiment the invention encompasses a dried, ready-to-eat pet food in the form of kibbles, each kibble comprising:
(i) a starch source which includes a protein source, wherein the starch source has a degree of gelatinization less than about 7.5 Joules/g of starch;
(ii) a coating or a filling containing one or more probiotic microorganisms.

In certain embodiments, the starch source is substantially non-gelatinized.

In certain embodiments, the coating or filling comprises a carrier substrate which contains the probiotic microorganism.

In certain embodiments, the carrier substrate is a fat, a protein digest, or a starch source, or a mixture thereof.

In certain embodiments, the pet kibble further includes a source of soluble fiber.

In certain embodiments, the pet kibble comprises a binding agent.

In certain embodiments, the binding agent is sodium alginate.

The pet food composition fed to the companion pet, for example canine and feline, is the standard normal diet fed to an animal. Table 1 is an illustrative diet of the invention for a canine or feline of 1 to 6 years of age.

TABLE 1

| Component | Amount (wt. % of dry matter) |
| --- | --- |
| Protein | 0-95% |
| Fat | 0-50% |
| carbohydrate | 0-75% |
| Probiotic (e.g., Lactobacillus alimentarius) | $1 \times 10^{14}$ cfu/g of food |

The quantities administered in the diet, all as wt % (dry matter basis) of the diet, are calculated as the active material, per se, that is measured as free material. The maximum amounts employed should not bring about toxicity.

In another embodiment, the invention encompasses a slow, sustained-release probiotic pet food composition. By using the composition of the invention in companion pets, it can be shown that an amount of probiotics can be delivered in a slow manner and can be maintained in the system for a longer period.

In certain embodiments, the food composition including probiotics include dry food pieces in the form of pellets, shaped protein pieces (e.g., extruded vegetable/animal proteins), or semi-moist pieces.

In another embodiment, pellets or pieces are made to resemble cheese or meat chunks. In other embodiments, the pet food pellets can be made from fibers such as cellulose, pellets of soy or corn meal, gelatin and/or animal by products, sugars and mixtures thereof.

In other embodiments, pellets can be made of rolled grains like oats or corn or made to resemble tortilla chip-like products. In other embodiments, pellets can include minerals, vitamins, and a filling agent, for example, protein, carbohydrate or fiber. In other embodiments, pellets can contain starch modified through enzymatic hydrolysis. In other embodiments, semi-moist pellets and pieces made of the above ingredients and mixtures thereof can be used as well.

In other embodiments, pellets with a starch source, texturized proteins, or semi-moist pieces can be produced using typical ingredients used to manufacture pet food such as grain sources (e.g., corn, rice, wheat, barley), protein sources (e.g., meat sources—poultry, beef, pork) vegetable sources (e.g., soy, corn gluten, casein, whey, eggs); fats (e.g., vegetable oils, animal fats, fish oils), plant fibers (beet pulp, soy hulls, cellulose) optionally vitamins (e.g., Vitamin E, C, B1, B2, B6); and minerals (e.g., calcium sources, phosphorus sources, salts, trace minerals) and various flavorants or palatants, processing aids, and preservatives to make a pet food that meets a pet's nutritional requirements and possesses the necessary aesthetic characteristics.

The pellets exhibit about 0.1 to about 0.8 $a_w$ and about 0.1 to about 15% moisture content.

The amount of probiotics included in the pet food composition is about $1 \times 10^4$ cfu (colony forming units)/g of food to about $1 \times 10^{14}$ cfu/g of food.

In certain embodiments, the probiotic pieces can be blended with other dry food for probiotic enrichment at an inclusion rate of 1-50%.

In certain embodiments, in addition to the probiotic, the pet food composition includes 0 to about 100 wt. % protein, 0 to about 100 wt. % fat, and 0 to about 100 wt. % carbohydrate.

In other embodiments, the pellets, texturized protein, or semi-moist pieces may be made in such a way that it would exhibit a density of 10-40 lbs/ft$^3$ and can be coated with fat, grease, or oil with palatant enhancers and other topical coating materials.

The present invention comprises a dry pet food containing less than about 15% moisture having a porous texture and appearance with fibrous food simulating pieces having a tough, pliable texture interspersed therein.

The pet food composition can also be in the form of snack products for companion animals. Snack products can include all manner of essentially two-dimensional shapes such as strips or ribbons (whether straight or curved), bowl or cup shaped (such as for use for dips or salsa) triangles, disks, squares or rectangles.

In another embodiment, the dried, ready-to-eat pet food pellet can be produced from any suitable ingredients such as those commonly used in dried, ready-to-eat pet food products. One of these ingredients is a starch source. Suitable starch sources are, for example, grain flours such as corn, rice, wheat, beets, barley, soy and oats. In addition, mixtures of these flours may be used. Rice flour, corn flour and wheat flour are particularly suitable either alone or in combination.

The starch source will be chosen largely based on the nutritional value, palatability considerations, and the type of cereal product desired.

In certain embodiments, pet composition products can also include a protein source. Suitable protein sources may be selected from any suitable animal or vegetable protein source, for example meat meal, bone meal, fishmeal, soy protein concentrates, milk proteins, gluten, and the like. The choice of the protein source will be largely determined by the nutritional needs, palatability considerations, and the type of cereal product produced. The starch source may also be a source of protein.

Methods of Making the Compositions of the Invention

In another embodiment, the invention encompasses a process of preparing a dried, ready-to-eat pet food, the process comprising making the pet food without heat (e.g., <60° C.) including a starch source and a protein source to form a starch matrix containing protein; forming the starch matrix into pieces; drying the pieces; and coating the pieces with a coating which contains one or more probiotic microorganisms.

In certain embodiments, the starch source and protein source are cooked without heat (<60° C.); extruded through an orifice; and then cut into pieces.

The probiotics can be added, for example, by one of the following methods:
(i) coating by applying onto the surface of the pet food a mixture of the probiotic microorganism including, for example, one of the lipid components of a coating system;
(ii) co-pelletizing the probiotic microorganism within the pet food (conducted at low temperature); or
(iii) dusting conducted by adding the probiotic microorganism onto the coating of the pet food.

In another embodiment, the invention encompasses a process of preparing a dried, ready-to-eat pet food, the process comprising cooking a starch source without heat (<60° C.), a protein source, and one or more probiotic microorganisms to form a starch matrix containing protein and one or more probiotic microorganisms; forming the starch matrix into pieces; and drying the pieces.

In certain embodiments, the starch source and protein source are cooked without heat (<60° C.); extruded through an orifice; and then cut into pieces.

In another embodiment, the invention encompasses a dried, ready-to-eat pet food composition comprising:
(i) a starch source comprising inulin and/or fructo-oligosaccharides;
(ii) a coating or filling comprising one or more probiotic microorganisms.

In another embodiment, the invention encompasses methods of promoting growth, preventing cell damage, and/or helping the body rid itself of harmful substances in a companion animal comprising administering to a companion animal a pet food composition including a slow, sustained-release amount of the one or more probiotic microorganisms to a companion animal.

Methods of Treating Disorders in Companion Animals

In another embodiment, the invention encompasses methods of maintaining or improving the health of the gastrointestinal tract, the skin and/or coat system or the immune system of a pet comprising the step of feeding a pet a pet food composition comprising a starch source and a live probiotic microorganism, wherein the starch source has a degree of gelatinization less than about 7.5 Joules/g of starch and wherein the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus,* or *Lactobaccillus*. In certain embodiments, the starch source is substantially non-gelatinized.

In another embodiment, the invention encompasses methods for the treatment and/or prophylaxis of disorders associated with the colonization of the gastrointestinal tract of pets by pathogenic micro-organisms, comprising the step of feeding a pet a pet food composition comprising a starch source and a live probiotic microorganism, wherein the starch source has a degree of gelatinization less than about 7.5 Joules/g of starch and wherein the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus,* or *Lactobaccillus*. In certain embodiments, the starch source is substantially non-gelatinized.

In another embodiment, the invention encompasses methods of regulating the immune response in pets, comprising the step of feeding a pet a pet food composition comprising a starch source and a live probiotic microorganism, wherein the starch source has a degree of gelatinization less than about 7.5 Joules/g of starch and wherein the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus,* or *Lactobaccillus*. In certain embodiments, the starch source is substantially non-gelatinized.

The invention also encompasses methods of ameliorating or reducing the effects of ageing in a pet comprising the step of feeding a pet a pet food composition comprising a starch source and a live probiotic microorganism, wherein the starch source has a degree of gelatinization less than about 7.5 Joules/g of starch and wherein the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus,* or *Lactobaccillus*. In certain embodiments, the starch source is substantially non-gelatinized.

In order to illustrate without unduly limiting the novel aspects of the present invention, the following examples are presented.

EXAMPLES

Example 1

This example describes the use of un-cooked pellets as carriers for probiotics. *Lactobacillus acidophilus* NCFM Danisco was the probiotic used in this study. The study was conducted as follows: 1) Study survival of *Lactobacillus acidophilus* NCFM added in the grain mix during production of pellets using cold pellet technology and regular extrusion conditions; 2) Produce pellets using cold pellet technology to coat them with *Lactobacillus acidophilus*; and 3) Study survival-ability of *Lactobacillus acidophilus* at 22° C. and 0.3 $a_w$.

Materials And Methods

Product Formulation:

Canine kibbles were used as a model for this study. Pellets were designed similar in composition and specifications to the kibbles. Pellets with probiotics added in the grain mix before extrusion and cold pellets with probiotics coated after extrusion were produced.

Materials:

*Lactobacillus acidophilus* NCFM ($1 \times 10^{11}$ cfu/g) Danisco (Madison Wis., 53716), Scogin HV Sodium Alginate FMC ByoPolymers (Philadelphia, Pa. 19103), Desiccators, and $MgCl_2$ (0.30 $a_w$).

Pellets with *Lactobacillus acidophilus* Added in Grain Mix:

Process:

a) Pellets made with probiotics with cold pellet and hot pellets extrusion process with conditions as in Example 2; b) Measured degree of gelatinization, moisture content, aw, density and durability of the above pellets. The degree of gelatinization of the test vs. control (grain mix feed mixture) must not be statistically significantly different.

Stability:

a) Compared probiotics survival-ability in pellets produced using the cold and hot extrusion process with processing conditions as in Example 2; conducted lactic acid bacteria counts of materials being processed both in the cold and hot process; and b) Coated pellets (cold and hot) as in current commercially available formula.

TABLE 2

Pellets with *Lactobacillus acidophilus* added in the Grain Mix Coated as canine kibbles

| Name | % | finished product Lbs |
|---|---|---|
| Cold Pellets | 84.740 | 33.896 |
| Animal Fat | 9.600 | 3.840 |
| Natural Flavor | 2.500 | 1.000 |
| Fish oil | 1.400 | 0.560 |
| Soybean Oil | 1.000 | 0.400 |
| Flavor Enhancer | 0.600 | 0.240 |
| Vit E | 0.160 | 0.064 |
| Total | 100.000 | 40.000 |

Coated as follows: Mixed all of the liquids, sprayed the mixture on the pellets, mixed for 5-10 minutes, and dispensed pellets into a multiwall bag. Made a blend of canine kibbles and pellets at 9:1 ratio. Placed 100 g samples* in plastic containers before setting them in desiccators equilibrated at ~0.30 $a_w$ ($MgCl_2$ saturated solution). Weighed 90 grams kibbles and 10 grams pellets with probiotics separately and placed them in the container. Desiccators were placed in a 22±3° C. chamber, and lactic acid bacteria counts were conducted every two weeks up to 3 months, and every month after that. Labeled the containers as CP (Cold pellets with Probiotics) and HP (Hot pellets with Probiotics).

Cold Pellets with *Lactobacillus acidophilus* Topically Coated Together with Soybean and Fish Oil.

Process:

a) Made pellets without probiotics in the grain mix using cold pellet extrusion process with conditions as in Example 2; and b) Measured degree of gelatinization, moisture content, aw, density and durability of the above kibbles.

Stability:

a) Coated cold pellets as in current commercially available formula

TABLE 3

Pellets with *Lactobacillus acidophilus* added with Soybean and Fish Oil Coated as canine kibbles

| Name | % | finished product Lbs |
|---|---|---|
| Cold Pellets | 84.640 | 33.856 |
| Animal Fat | 9.600 | 3.840 |
| Natural Flavor | 2.500 | 1.000 |
| Fish Oil | 1.400 | 0.560 |
| Soybean Oil | 1.000 | 0.400 |
| Flavor Enhancer | 0.600 | 0.240 |
| Vit E | 0.160 | 0.064 |
| *L. acidophilus* NCFM | 0.100 | 0.040 |
| Total | 100.000 | 40.000 |

Coated as follows: Mixed Animal Fat+Natural Flavor+Flavor Enhancer+Vit E, coated pellets with the mixture above for 5-10 minutes at RT, mixed *Lactobacillus acidophilus* NCFM with the soybean oil and fish oil and coated the pellets with the mixture, sprayed mixture at 22 psi, mixed for 5-10 minutes and dispensed pellets into a multiwall bag. Made a blend of kibbles and pellets at 9:1 ratio. Placed 100 g samples (weighed 90 grams kibbles and 10 grams pellets coated with probiotics separately) in plastic containers before setting them in desiccators equilibrated at ~0.30 $a_w$ ($MgCl_2$ saturated solution). Desiccators were placed in a 22±3° C. chamber, and lactic acid bacteria counts were conducted every two weeks for 22° C. up to 3 months, and every month after that. Labeled containers as CCP (Cold pellets coated with Probiotics)

The Following Measurements were Made:

Starch Gelatinization—DSC (Differential Scanning calorimetry) analysis was conducted to determine starch gelatinization. Samples were soaked with a 2:1 water pet food ratio for approximately 2 hrs at room temperature and then scanned from 10° C. to 100° C. with a 10° C./min scanning rate in a Perkin Elmer DSC.

Moisture content

Water activity (aw)

Density

PDI (Pellet Durability Index)

Probiotics Count Method

Procedure for Probiotics Count Method: 1) Aseptically weigh 25 g of kibbles-pellets mixture into a sterile stomacher bag; 2) Aseptically add 225 g of sterile, room temperature, Difco MRS broth to the 25 g of kibbles-pellets mixture; 3) Turn stomacher on and allow the kibbles-pellets and broth blend for two minutes; 4) Hold the sample at room temperature for 30 minutes to rehydrate the kibbles-pellets; 5) Return the sample to the stomacher and blend for an additional two minutes; 6) Make a serial dilution in 99 ml 0.1% peptone dilution blanks by adding 1 ml of the primary 10^1 dilution (from the stomacher bag) to obtain 10^3 dilution. Repeat this operation until the desired dilution series is obtained. Shake dilution bottles as directed in Standard Methods for the Examination of Dairy Products, 16th Edition, 1992, Chapter 6 (Microbiological Count Methods), pages 213-246; 7) Proceeding in triplicate, transfer 1 mL of each appropriate dilution to labeled, sterile Petri plates with sterile 1 mL pipettes; 8) Take a bottle of sterile Difco MRS agar that has been melted (100 C for 30 minutes)

and tempered to 45 C in a 45 C water bath and sterilize the bottle by dipping it into a 200 PPM chlorine solution (made fresh daily), or by flaming the lip of the bottle; 9) Under a laminar hood, aseptically add 1 mL of sterile 5% cysteine-HCl solution to each 100 mL of the Difco MRS agar to achieve a final cysteine-HCl concentration of 0.05% in the MRS agar; 10) Pour approximately 15 mL of the MRS/0.05% cysteine-HCl agar into each plate. Swirl the plates to mix, and let solidify at room temperature on a cool level surface; 11) Incubate the plates at 38 C under anaerobic conditions (BD GasPak EZ Container Systems with indicator in an anaerobic jar) for 72 hours; and 12) Count colonies on the MRS/0.05% cysteine-HCl agar plates and record as viable cell count per gram, taking into account the dilution factor of the plates counted.

Results

Finished products (cold and hot pellets) were analyzed for moisture, water activity density and durability (Table 4).

Figure 1:
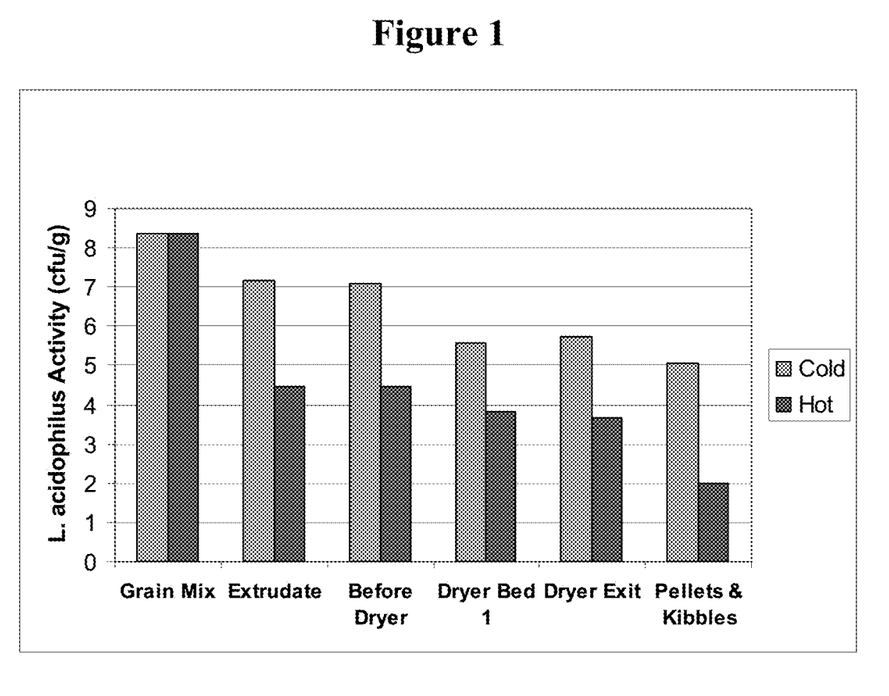
FIG. 1 illustrates *Lactobacillus acidophilus* activity during cold processes compared to hot processes of exemplary embodiments of the invention. *Lactobacillus acidophilus* activity added to the grain mix was monitored during hot and cold extrusion process. It was shown that the *Lactobacillus acidophilus* activity is 2-3 logs less during the steps of the cold versus hot processing.

*Lactobacillus acidophilus* activity added to the grain mix was monitored during hot and cold extrusion process. It was shown that the *Lactobacillus acidophilus* activity is 2-3 logs less during the steps of the cold versus hot processing (FIG. 1).

Figure 2:
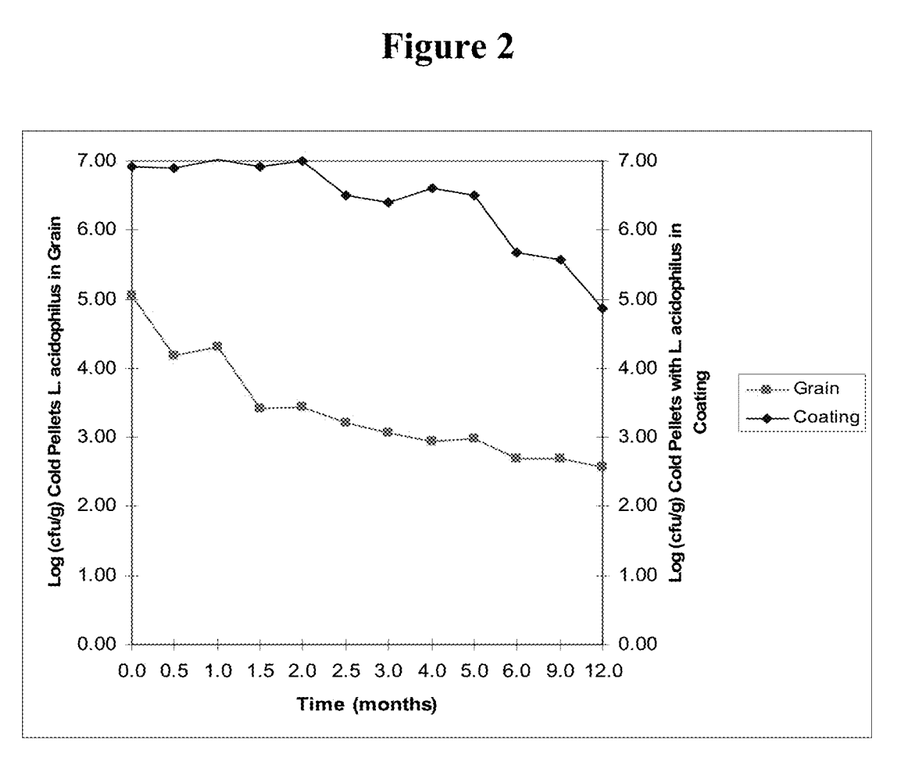
FIG. 2 illustrates cold pellets with *L. acidophilus* added in the grain mix before extrusion and cold pellets coated with *L. acidophilus* and mixed with canine kibbles (1:9) at 22° C. and 0.3 $a_w$ In certain embodiments, better retention of *L. acidophilus* was observed when added in the coating than when added in the grain mix before extrusion. It was shown that the *L. acidophilus* activity is 2 logs higher after processing in the coating than when added in the grain mix before extrusion. The *L. acidophilus* activity after 12 month storage is 1.5 logs higher.

Better retention of *Lactobacillus acidophilus* was observed when added in the coating than when added in the grain mix before extrusion. It was shown that the *Lactobacillus acidophilus* activity is 2 logs higher after processing in the coating than when added in the grain mix before extrusion. The *Lactobacillus acidophilus* activity after 12 month storage is 1.5 logs higher (FIG. 2).

Figure 3:
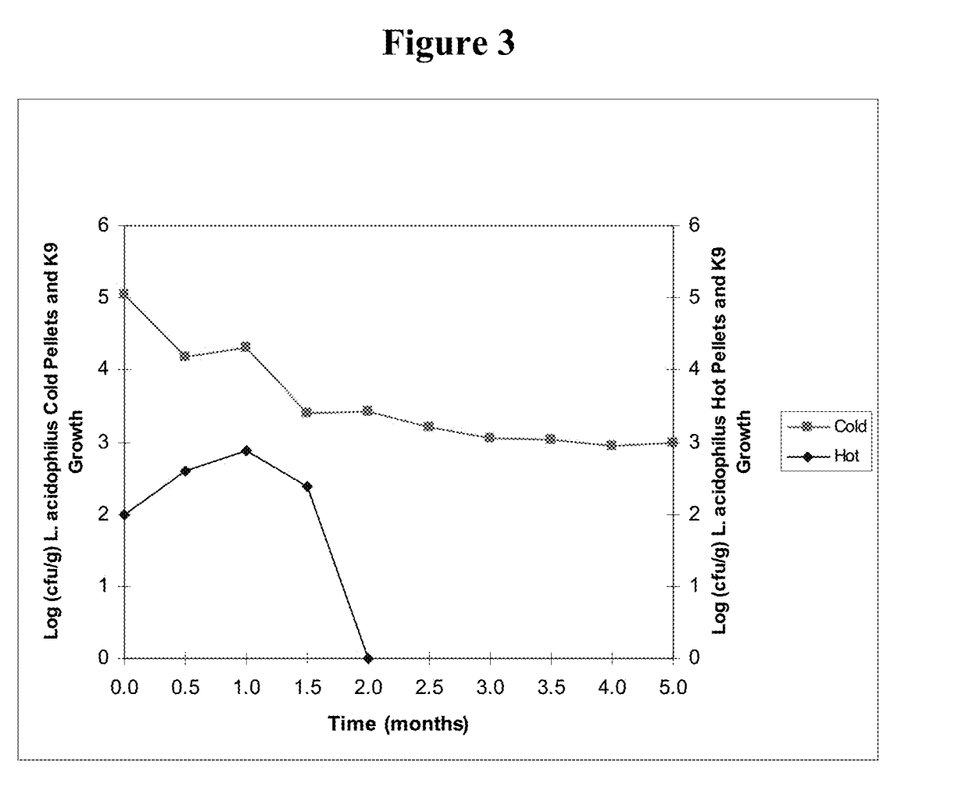
FIG. 3 illustrates cold and hot pellets with *L. acidophilus* added to grain mix before extrusion and mixed with canine kibbles (1:9) at 22° C. and 0.3 aw. *L. acidophilus* lost only 2 logs of activity within 5 months in cold pellets where as in hot pellets it was completely destroyed in 2 months. The cold pellets provide a more stable environment for the probiotics both in process and storage for exemplary embodiments of the invention.

The *Lactobacillus acidophilus* activity was almost 2 logs less within 5 months in cold pellets where as in hot pellets, the *Lactobacillus acidophilus* activity was completely destroyed in 2 months (FIG. 3).

TABLE 4

Cold and Hot Pellets Analysis

| | Analyte | | |
|---|---|---|---|
| | Cold Pellets No Probiotic in Grain Mix | Cold Pellets Probiotic in Grain Mix | Hot Pellets Probiotic in Grain Mix |
| | Finished Product Average ± Std. dev | Finished Product Average ± Std. dev | Finished Product Average ± Std. dev |
| Moisture (%) | 7.88 ± 0.1 | 7.58 ± 0.08 | 7.51 ± 0.15 |
| aw | 0.33 ± 0.04 | 0.37 ± 0.00 | 0.38 ± 0.01 |
| Density (Lbs/ft$^3$) | 33.20 ± 0.28 | 33.20 ± 0.14 | 33.20 ± 0.14 |
| Durability (% Not broken) | 97.80 ± 0.07 | 97.80 ± 0.10 | 97.80 ± 0.10 |

Starch Gelatinization was determined for Cold Pellets as ~7.5±2.4 Joules/g of starch by DSC. It has been reported that corn starch gelatinization ranges from 7.5-11.6 Joules/g of starch (Ji et al, 2004). Table 5 shows that results are not statistically significant different (ttest) for grain mix versus cold pellets with or without probiotics in the grain mix. Thus, the starch in the grain mix was intact through the extrusion process using cold conditions. However, current extrusion conditions (hot process) did not show any DSC gelatinization enthalpy because the starch was gelatinized during extrusion.

TABLE 5

Cold and Hot Pellets Starch Gelatinization Results

| | Corn Starch Gelatinization (Joules/g of starch) | | |
|---|---|---|---|
| Sample | Grain Mix | Finished Product | ttest |
| Cold Pellets w/o Probiotics in grain mix | 7.0 ± 2.3 | 7.5 ± 2.4 | 0.5792 |
| Cold Pellets with Probiotics in grain mix | 6.8 ± 2.0 | 7.4 ± 2.4 | 0.5036 |
| Hot Pellets with Probiotics in grain mix | 6.8 ± 2.0 | Gelatinized | — |

Based on the above results cold pellets with and without probiotics in the grain mix were produced without gelatinized starch. Thus, survival-ability of *Lactobacillus acidophilus* in these pellets was assessed.

Example 2

Cold Pellets with Probiotics Process

Ingredients:

1) Grain Mix (Pass at least 50 Lbs of soybean meal thru screen number 4 (4/64") opening, pass all the rest of the ingredients thru screen number 4 (4/64") opening and keep 2-3 Lbs of grain mix); 2) Mix Probiotics with Soybean Meal (Use 40 Lbs of soybean meal passed thru screen number 4 (4/64") opening, mix the probiotics (4.232 Lbs) with the 40 Lbs of soybean meal (passed thru screen number 4) in a cement mixer for 5 minutes by adding 20 Lbs of the soybean meal to the cement mixer, adding the probiotics (4.232 Lbs), adding 20 Lbs of the soybean meal to the cement mixer, mixing for 5-10 minutes and dividing the mixture in 2 parts (22.116 Lbs); 3) Mix the mixture of the soybean meal and probiotics with the grain mix (Divide 4200.8 Lbs of grain mix in 2 parts of 2100.4 Lbs, mix Grain with Probiotics in a 2000 Lbs Wenger Ribbon blender (Wenger, Sabetha, Kans.) by adding half of the grain mix (1050.2 Lbs) to the ribbon blender, adding the soybean meal and probiotics mixture (22.116 Lbs), adding the other half of the grain mix (1050.2 Lbs), mixing for 15 minutes and after mixing, convey the blend (grain mix and probiotics) from the mixer through the 50 hp hammer mill auger system into 4 totes, remove the hammer mill screen and do not run the mill and repeat this 1 more time); 4) Gel binder preparation—2.5% FMC sodium alginate prepared as follows: Weigh 37.5 Lbs of sodium alginate to prepare 2.5% solution for 4200.8 Lbs of grain, based on 300 Lbs batch prepare 5 batches of a 2.5% sodium alginate solution, weigh water (292.5 lbs) into the kettle in the tri-blender system, not heated, as water is pumped thru the Waukasha pump, at maximum speed, the sodium alginate (7.5 lbs) is added to the tri-blender and mixes with the water completely, hen the water and dry ingredient are mixed completely, the mixture is pumped in to a barrel and mix with the homogenizer mixer for approx 10 minutes or until gel is achieved. The solution will be added into the pre-conditioner and a sample of the solution is kept.

Extrusion:

Product temperature should not exceed 60-70° C. (140° F.) for Cold Pellets and for Hot pellets use regular extrusion conditions.

Drying:

Product temperature should be kept below 70° C. (158° F.) for Cold Pellets and for Hot pellets use regular drying conditions.

Finished Product Specifications:

Moisture 7-8% ($a_w$=0.3); Density 25-35 Lbs/ft$^3$

Example 3

Cold Pellets without Probiotics Process:

1) Grain Mix (Pass all of the ingredients thru screen number 4 (4/64") opening and keep 2-3 Lbs of grain mix); 2) Gel binder preparation—2.5% FMC sodium agitate prepared as follows: Weigh 37.5 Lbs of sodium alginate to prepare 2.5% solution for 4200.8 Lbs of grain, based on 300 Lbs batch prepare 5 batches of a 2.5% sodium alginate solution, weigh water (292.5 lbs) into the kettle in the tri-blender system, not heated, as water is pumped thru the Waukasha pump, at maximum speed, the sodium alginate (7.5 lbs) is added to the tri-blender and mixes with the water completely, hen the water and dry ingredient are mixed completely, the mixture is pumped in to a barrel and mix with the homogenizer mixer for approx 10 minutes or until gel is achieved. The solution will be added into the preconditioner and a sample of the solution is kept.

Extrusion:

Product temperature should not exceed 60-70° C. (140° F.).

Drying:

Product temperature should be kept below 60-70° C. (158° F.).

Finished Product Specifications:

Moisture 7-8% ($a_w$=0.3); Density 25-35 Lbs/ft$^3$

It is realized the variations in these and related factors could be readily made within the concept taught herein.

What is claimed is:

1. A method for maintaining the health of a gastrointestinal tract of a companion pet in need thereof, comprising, administering an effective amount of a pet food composition consisting of a starch source, a binding agent, ingredients to meet the nutritional requirements for the companion animal in need thereof, and a topical coating,
   wherein maintaining the health of the gastrointestinal tract of the companion pet in need thereof comprises treating or preventing disorders associated with the colonization of the gastrointestinal tract of the companion pet by pathogenic microorganisms,
   wherein the pet food composition are semi-moist pellets,
   wherein the binding agent consists of sodium alginate,
   wherein the topical coating consists of a live probiotic microorganism, fish oil, and soybean oil,
   wherein the starch source has a degree of gelatinization less than about 7.5 Joules/g of starch, and,
   wherein the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus,* or *Lactobaccillus*.

2. The method of claim 1, wherein the starch source is substantially non-gelatinized.

3. The method of claim 1, wherein the live probiotic microorganism is present in an amount of from about $10^4$ cfu/g to about $10^{14}$ cfu/g of pet food, based on a total weight of the pet food composition.

4. The method of claim 1, wherein the pet food composition is a dog food.

5. The method of claim 1, wherein the pet food composition is a cat food.

6. The method of claim 1, wherein the live probiotic microorganism is *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus bulgaricus Lactobacillus acidophilus, Lactobacillus alimentarius, Lactobacillus casei* subsp. *casei, Lactobacillus casei Shirota, Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus reuteri, Lactobacillus rhamnosus (Lactobacillus GG), Lactobacillus sake, Lactobacillus sporogenes, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Streptococcus faecium, Staphylococcus carnosus, Leuconostoc mesenteroides* ssp *cremoris, Pediococcus acidolactici, Pediococcus cerevisiae, Bifidobacterium bifidus, Bifidobacterium longum, Brevibacterium linens, Propionibacterium shermanii, Propionibacterium arabinosum, Penicillium camembertii,* or *Staphylococcus xylosus*.

7. The method of claim 1, wherein the pet food composition is cooked without heating to a temperature of 60° C. or greater.

8. A method for maintaining the health of a gastrointestinal tract of a companion animal in need thereof, comprising, administering an effective amount of a pet food composition consisting of ingredients to meet the nutritional requirements for the companion pet, a starch source, and a topical coating,
   wherein maintaining the health of the gastrointestinal tract of the companion pet in need thereof comprises treating or preventing disorders associated with the colonization of the gastrointestinal tract of the companion pet by pathogenic microorganisms,
   wherein the topical coating consists of a live probiotic microorganism, soybean oil, and fish oil,
   wherein the pet food composition are semi-moist pellets, and
   wherein the live probiotic microorganism is one or more of the genera: *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus,* or *Lactobaccillus*.

\* \* \* \* \*